United States Patent
Bruck et al.

(10) Patent No.: US 9,255,915 B2
(45) Date of Patent: Feb. 9, 2016

(54) EVALUATING A PROCESS EFFECT OF SURFACE PRESENTATION ANGLE

(71) Applicants: Gerald J. Bruck, Oviedo, FL (US);
Brandon W. Shinn, Houston, TX (US);
Ahmed Kamel, Orlando, FL (US)

(72) Inventors: Gerald J. Bruck, Oviedo, FL (US);
Brandon W. Shinn, Houston, TX (US);
Ahmed Kamel, Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 422 days.

(21) Appl. No.: 13/799,092

(22) Filed: Mar. 13, 2013

(65) Prior Publication Data
US 2013/0298703 A1 Nov. 14, 2013

Related U.S. Application Data

(63) Continuation of application No. 61/645,824, filed on May 11, 2012.

(51) Int. Cl.
| | |
|---|---|
| *G01N 33/00* | (2006.01) |
| *B23K 37/04* | (2006.01) |
| *B23K 31/12* | (2006.01) |
| *G01N 3/58* | (2006.01) |

(52) U.S. Cl.
CPC .............. *G01N 33/00* (2013.01); *B23K 31/12* (2013.01); *B23K 37/0408* (2013.01); *B23K 37/0452* (2013.01); *G01N 3/58* (2013.01)

(58) Field of Classification Search
None
See application file for complete search history.

(56) References Cited

U.S. PATENT DOCUMENTS

| | | | |
|---|---|---|---|
| 5,854,433 A * | 12/1998 | Patel et al. ................... 73/865.6 |
| 6,078,384 A | 6/2000 | Dammann et al. |
| 6,125,693 A | 10/2000 | Dubois |
| 8,045,184 B2 | 10/2011 | Kawakami et al. |

FOREIGN PATENT DOCUMENTS

| | | |
|---|---|---|
| DE | 19962967 A1 | 7/2001 |
| EP | 1577727 A1 | 9/2005 |
| FR | 2629668 A1 | 10/1989 |

OTHER PUBLICATIONS

Lin, J. and B. Hwang. Coaxial Laser Cladding on an Inclined Substrate. Optics and Laser Technology, (Abstract) 1999.
J. Lin and B. Hwang. Clad Profiles in Edge Welding Using a Coaxial Powder Filler Nozzle. Optics and Laser Technology, (Abstract), 2001.

(Continued)

*Primary Examiner* — Robert R Raevis

(57) ABSTRACT

An apparatus (10) and method for evaluating an effect of a surface presentation angle (A). The apparatus supports a plurality of samples (12) separated by support plates (18) between end plates (22) in a shish kebab arrangement. A groove (34) is formed on each side of each support plate for receiving an edge of each respective sample at a different angle relative to an axis of impingement (32). A clamping mechanism (20) holds the end plates, support plates and samples together in the fixed orientation exposing each sample surface at a different presentation angle, yet at the same distance from a process end effector (30). The sample impingement surfaces are exposed to the process, and the effect of the different surface presentation angles is determined from the samples. Process variables to counter the effects of surface presentation angle may be identified and controlled.

16 Claims, 2 Drawing Sheets

(56) References Cited

OTHER PUBLICATIONS

M. Brandt, J. Harris, and C. Chipperfield. In-situ Laser Repair of Steam Turbine Blades. Proceedings of the 4th International WLT-Conference on Lasers in Manufacturing 2007, Munich, Jun. 2007.

G.J. Bruck, J.E. Smith, J.I. Nurminen. A Study of the Effect of Angle of Beam Incidence on Laser Transformation Hardening of 4340 Alloy Steel. Westinghouse R&D Center, Pittsburgh, Oct. 11, 1984 (84-1D4-LAGER-P1).

* cited by examiner

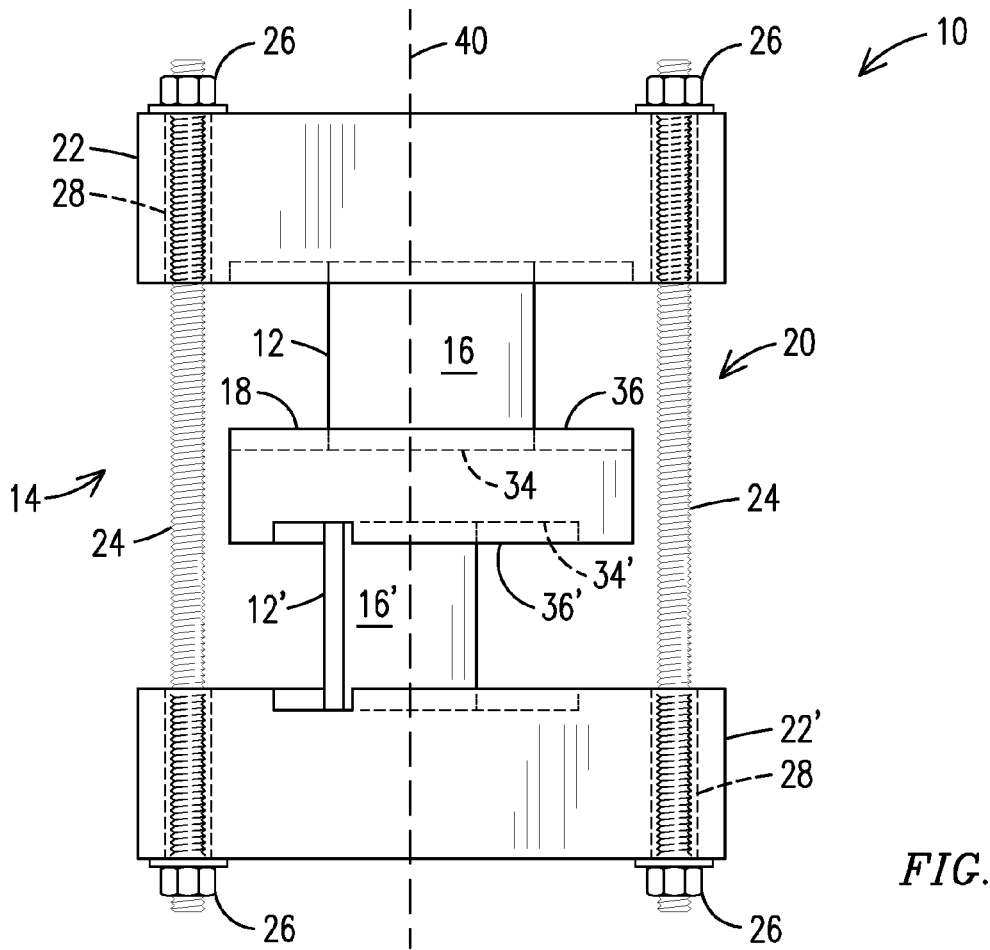
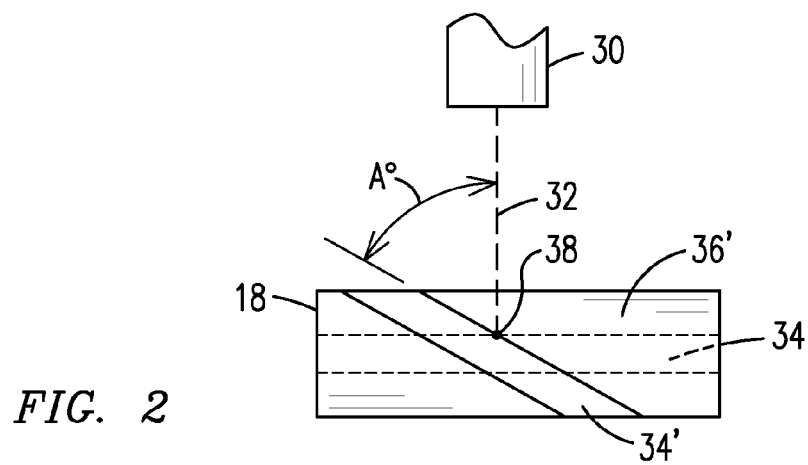

EVALUATING A PROCESS EFFECT OF SURFACE PRESENTATION ANGLE

This application claims benefit of the 11 May 2012 filing date of U.S. provisional patent application No. 61/645,824 which is incorporated by reference herein.

FIELD OF THE INVENTION

This invention relates generally to the field of metrology.

BACKGROUND OF THE INVENTION

Energy beams such as laser or electron beams are known to be used as a heat source for certain manufacturing and repair processes such as welding, hard-facing and overlay coating, such as may be used during the repair of gas turbine engine components. The angle of incidence of the energy beam is an important variable that affects the quality of the process. The American Society of Mechanical Engineers (ASME) Boiler and Pressure Vessel Code Section IX identifies a change of more than ±10 degrees in the relative angle between the axis of the beam and the impinged work piece surface (angle of incidence) as an essential variable for such processes. Angled surfaces cause an otherwise focused and maximum power density beam to be spread over a broader surface having an elliptical rather than round shape. Moreover, the effect of gravity varies as a surface undergoing a process is inclined from horizontal, and such changes may adversely affect processes utilizing a molten weld pool or powders. Relatively little work has been published to quantify these effects for material and/or heat additive processes.

BRIEF DESCRIPTION OF THE DRAWINGS

The invention is explained in the following description in view of the drawings that show:

FIG. 1 is a plan view of an embodiment of an apparatus for evaluating an effect of surface presentation angle.

FIG. 2 is a side view of the support plate of the apparatus of FIG. 1 and an energy source as they may be relatively positioned during a process.

DETAILED DESCRIPTION OF THE INVENTION

Figure 3:
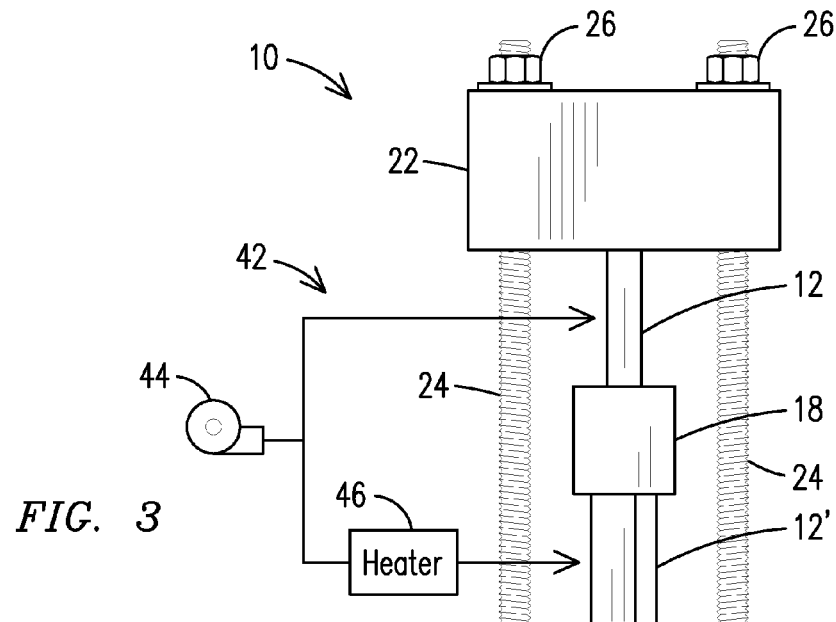
FIG. 3 is a side view of the apparatus of FIG. 1 with a schematic illustration of a temperature control system for the samples.

The term "surface presentation angle" is used generally herein to describe the orientation of a surface undergoing a process relative to a reference direction, such as relative to an angle of incidence of an energy beam or relative to horizontal.

The present invention is useful for evaluating the effect of surface presentation angle for material and/or heat additive processes such as laser or electron beam welding, laser hard-facing overlay, laser corrosion-resistant overlay, etc. The present invention provides a device that fixtures an array of samples at a variety of different, known, and controlled surface presentation angles such that a single pass of a processing device produces a full complement of processed test samples. By holding process variables constant as the process progresses over the differently angled surfaces, the effect of surface presentation angle can be demonstrated. Alternatively, by varying process variables for each differently angled surface, a process can be qualified to produce consistent results across a range of surface presentation angles.

FIG. 1 illustrates one embodiment of an apparatus 10 for evaluating an effect of surface presentation angle. FIG. 1 is a simplified embodiment of the invention utilizing only two samples. While this simplified embodiment is useful for illustration and discussion purposes, one skilled in the art will recognize that more than two samples may be preferred for evaluating the effect of surface presentation angle over a wider range of angles. The apparatus 10 illustrates two samples 12, 12' and a fixture 14 supporting the samples 12, 12' in fixed relative orientations presenting their respective impingement surfaces 16, 16' at respective different angles. The fixture 14 includes a support plate 18 disposed between the samples 12, 12'. The fixture also includes a clamping mechanism 20 compressing two end plates 22, 22' together to hold the support plate 18 and samples 12, 12' together in fixed relative positions. In this embodiment, the clamping mechanism 20 includes two threaded rods 24 held in tension by nuts 26 threaded onto ends of the rods 24 for urging the end plates 22, 22' toward each other. The rods 24 pass through holes 28 in the end plates 22, 22'. In other embodiments, the samples may be larger and may also include holes for accommodating passage of the rods 24.

One skilled in the art will appreciate that other forms of clamping mechanisms may be used to urge the apparatus together, for example C-clamps, bolts with a fixed heads, partially or intermittently threaded rods, spring-loaded devices, rods with a nut welded in place on one end, etc.

FIG. 2 is a side view of the support plate 18 illustrating how the samples are held at the appropriate angles. FIG. 2 illustrates an energy source 30 and an axis of impingement 32 of an energy beam from the energy source 30 as may be present when the apparatus 10 is used during a material and/or heat additive process. Support plate 18 includes a respective groove 34, 34' formed on each of two opposed sides 36, 36' for receiving the respective sample 12, 12'. In the embodiment of FIG. 2, groove 34 (illustrated in phantom because it is on the hidden side 36) is formed to have a longitudinal orientation that is generally horizontal and perpendicular to the impingement axis 32. Groove 34' is formed to have a longitudinal orientation that is angled from the horizontal such that impingement surface 16' will have an angle of incidence A° relative to the impingement axis 32. Edges of the respective samples 12, 12' are engaged within the grooves 34, 34' to position the samples 12, 12' to have the desired surface presentation angles (i.e. 90° for sample 12 and A° for sample 12' in the illustrated embodiment). Note that the end plates 22, 22' are illustrated in FIG. 1 as also having corresponding grooves for receiving the opposed edges of the samples 12, 12'. In various embodiments, such grooves may be provided only in the end plates, only in the support plate, or in both, as required to provide a desired degree of positional accuracy and support for the samples 12, 12'. Other embodiments may have more than two samples, with grooves formed to present the sample impingement surfaces at angles such as 15°, 30°, 45°, 60°, 75°, and 90° for example.

In FIG. 2 there is illustrated a point 38 which establishes a fixed distance along the axis of impingement 32 from the energy source 30. The grooves 34, 34' are both formed such that the respective impingement surfaces 16, 16' of samples 12, 12' are held at this fixed distance from the energy source 30 along the axis of impingement 32 by the apparatus 10 as the energy source 30 moves relative to the apparatus 10 during a process. As the energy source 30 is moved relative to the apparatus 10, there is established a line of intersection 40 between the energy beam and the samples 12, 12' as illustrated in FIG. 1, and that line 40 appears as a point 38 in the side view of FIG. 2 seen perpendicular to the axis of impingement 32. By maintaining a fixed distance between the energy source 30 and the line of intersection 40 along the samples 12, 12', the change in energy flux at the impingement surfaces 16, 16' is isolated to the effect of the surface presentation angle A° verses surface presentation angle 90° only. The grooves 34, 34' are formed such that line of intersection 40 can be considered as an axis of rotation when moving from one sample 12 to the next sample 12' so that the surfaces 16, 16' are each presented at an equal distance from the energy source 30.

One skilled in the art will appreciate that the relative motion between the apparatus 10 and the energy source 30 (or other process device) may be accomplished by moving the apparatus 10 or the energy source 30 or both. Apparatus 10 not only fixes the samples in their relative orientations, but the presence of the support plate 18 between the samples 12, 12' also provides a degree of physical isolation of the samples 12, 12' as they individually and consecutively undergo the process as the energy source 30 is traversed relative to the apparatus 10. The apparatus 10 may be formed of steel, aluminum or other suitable metal, and in one embodiment, the support plate 18 may include a ceramic material to provide additional thermal isolation between samples 12, 12'. This may be useful when it is desired to maintain the two samples 12, 12' at different temperatures during the process and when it is important to ensure that processing of one of the samples does not unintentionally affect (e.g. preheat) a second subsequent sample's processing. FIG. 3 illustrates a side view of the apparatus 10 and a temperature control system 42 which includes a fan 44 for directing unheated air across sample 12 and for directing air through a heater 46 and then across sample 12'. Such an arrangement facilitates the collection of data correlating the effect of sample temperature on the process in conjunction with the effect of surface presentation angle. Other temperature control systems may be envisioned, such as electrical resistance heaters applied to at least one sample, the use of a chiller to cool air passing over a sample, induction coils, water cooled chill blocks, etc.

Figure 4:
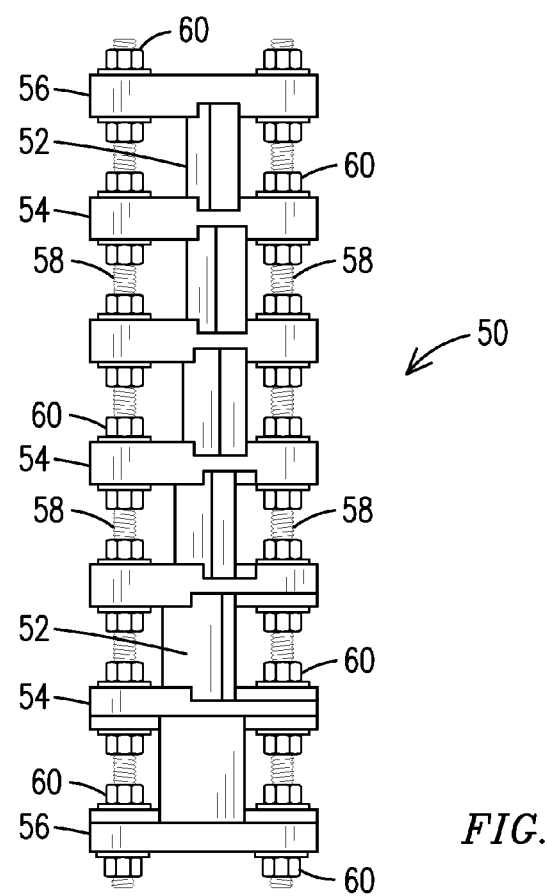
FIG. 4 is a plan view of another embodiment of an apparatus for evaluating an effect of surface presentation angle.

FIG. 4 illustrates an apparatus 50 wherein six samples 52 are fixtured at six different surface presentation angles, as compared to the two samples of FIG. 1. The support plates 54 and end plates 56 of FIG. 4 have like dimensions so that the threaded rods 58 pass through each of the plates 54, 56, forming a structure that can be described as a "shish kebab" of alternating samples and plates disposed along the rods. In this embodiment, nuts 60 are provided on each side of each plate 54, 56, with each nut 60 urged against a respective plate to hold the plate in a fixed position relative to the rod and relative to adjacent plates. The provision of nuts 60 on both sides of each plate provides an added degree of fixturing precision for constraining dimensional variations that might otherwise be introduced by normal machining tolerances.

Other embodiments of the invention may incline the samples to either or both sides of the plane of processing (the plane established by the axis of impingement and travel motion). Furthermore, angles may be inclined to a side toward or away from the axis of impingement within the plane of processing.

In use, the apparatus 10, 50 is assembled to support the samples, and it is then positioned on a work table in proximity to a process end effector, such as a laser beam and powder disbursement nozzle. The process is then activated and the end effector is moved across the apparatus such that the process, for example laser cladding, is performed on each of the samples consecutively. The process may be temporarily interrupted as the end effector passes over the end plates and support plates. One or multiple passes of the process may be made over the samples. The apparatus is then disassembled and the samples are inspected to determine the results of the process. If the process variables were held constant, the effects of surface presentation angle will be demonstrated in the samples. The process may be evaluated to determine process variables that can be changed to counteract the effect of surface presentation angle. A set of samples may be exposed to the process with such variables being appropriately controlled as the end effector functions over each respective sample across the apparatus. If such samples demonstrate process results within a desired degree of similarity among the samples, the process can be qualified for use within the demonstrated range of surface presentation angles. In this manner, fundamental investigations may be made to quantify the effects of surface presentation angle alone or in conjunction with other sample and process attributes, for example but not limited to the following:

| PROCESS | ATTRIBUTE |
|---|---|
| laser transformation hardening | surface roughness coatings to absorb the laser beam |
| laser welding | reflectivity effect on penetration reflectivity effect on plasma suppression gas gravitational effect on molten pool |
| electron beam welding | charging effects deflecting the electron beam power density changes affecting penetration |
| laser cladding | gravitational effects reflectivity effect on powder capture efficiency reflectivity effect on dilution from the substrate |
| water jet cutting | deflection of water stream affecting cut quality |

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. An apparatus for evaluating an effect of a surface presentation angle, the apparatus comprising:
   opposed end plates and a support plate disposed there between;
   a first groove formed on a first side of the support plate for receiving an edge of a first sample therein at a first angle relative to an axis of impingement; and
   a second groove formed on a second side of the support plate opposed the first side for receiving an edge of a second sample therein at a second angle, different than the first angle, relative to the axis of impingement; and
   a clamping mechanism for urging the end plates together with the support plate and first and second samples disposed there between during a process to hold the samples at their respective different angles relative to the axis of impingement such that a surface presentation angle of the first sample is different than a surface presentation angle of the second sample.

2. The apparatus of claim 1, wherein relative movement between the apparatus and the axis of impingement defines a line of impingement along each sample; and further comprising:
   the first and second grooves being formed such that when the apparatus is viewed from a side in a direction perpendicular to the axis of impingement, the lines of impingement along each sample are aligned at a same point on the axis of impingement to maintain the lines of impingement at the same point on the axis of impingement.

3. The apparatus of claim 1, wherein the clamping mechanism comprises a threaded rod passing through openings in the end plates and at least one nut threaded onto the rod and placing the rod into tension to urge the end plates together.

4. The apparatus of claim 3, further comprising:
a hole formed in the support plate and the rod passing through the support plate hole; and
a groove formed in a side of each end plate for receiving an opposed edge of the respective sample therein.

5. The apparatus of claim 4, further comprising a nut threaded onto the rod on each opposed side of the support plate and affixing the support plate there between relative to the rod and relative to the end plates.

6. The apparatus of claim 1, wherein the support plate comprises a ceramic material.

7. The apparatus of claim 1, further comprising a temperature control system for maintaining the first sample at a temperature different than a temperature of the second sample during the process.

8. The apparatus of claim 1, wherein the clamping mechanism comprises a threaded rod passing through respective openings in the end plates and the support plate, and a nut threaded onto the rod on each side of each of the end plates and support plate to affix the plates relative to the rod and relative to each other.

9. An apparatus for evaluating an effect of a surface presentation angle, the apparatus comprising:
a plurality of samples each comprising a respective impingement surface; and
a fixture supporting the plurality of samples in fixed relative orientations presenting their respective impingement surfaces at respective different angles relative to an axis of impingement, wherein each impingement surface defines a respective perimeter, and wherein in the fixed relative orientations a line of intersection passes through two points of each perimeter;
wherein the fixture further comprises:
a support plate separating each adjacent pair of the samples; and
a clamping mechanism compressing the samples and each support plate together in fixed relative positions.

10. The apparatus of claim 9, further comprising:
an end plate at each end of the apparatus disposed against respective end samples;
a groove formed in a side of each end plate and on each opposed side of each support plate for receiving respective edges of the respective sample, the grooves formed at respective angles relative to the axis of impingement effective to present the respective impingement surfaces at their respective different angles relative to the axis of impingement.

11. The apparatus of claim 9, further comprising grooves formed on opposed sides of the support plate, each groove formed at one of the respective different angles relative to the axis of impingement, such that when edges of the samples are disposed within the respective grooves, the impingement surfaces are presented at their respective different angles relative to the axis of impingement.

12. The apparatus of claim 11, further comprising the grooves formed such that when the apparatus is moved along an axis perpendicular to the axis of impingement, all of the impingement surfaces intersect the axis of impingement at a same point.

13. The apparatus of claim 9, wherein the clamping mechanism further comprises:
a hole formed in each support plate;
a rod passing through the holes; and
a nut threaded onto the rod on each opposed side of each support plate for affixing the respective support plate there between relative to the rod.

14. The apparatus of claim 9, further comprising a shish kebab structure wherein the samples are adjacently disposed along a rod.

15. A method for evaluating an effect of a surface presentation angle, the method comprising:
securing a plurality of samples within a fixture supporting the samples in fixed relative orientations presenting their respective impingement surfaces at respective different angles relative to an axis of impingement;
moving an end effector past the fixture and samples to expose each respective impingement surface in succession to a process; and
evaluating the samples to determine an effect of the different surface presentation angles.

16. The method of claim 15, further comprising controlling a process variable in response to the surface presentation angle of the respective impingement surfaces to counter the effect of the surface presentation angle.

* * * * *